United States Patent
Colman

[19]

[11] Patent Number: 5,938,631
[45] Date of Patent: Aug. 17, 1999

[54] METHOD FOR JOINT TAPING WITH INELASTIC TAPE

[76] Inventor: John P. Colman, 14566 El Puente Way, Saratoga, Calif. 95070

[21] Appl. No.: 09/007,968

[22] Filed: Jan. 16, 1998

Related U.S. Application Data

[63] Continuation-in-part of application No. 08/753,149, Nov. 20, 1996, abandoned.

[51] Int. Cl.⁶ .............................. A61F 13/00; A61F 5/00
[52] U.S. Cl. ................................................ 602/75; 602/76
[58] Field of Search ................................ 602/41–59, 8–9; 206/411, 440, 441; 428/236, 225, 241, 261

[56] References Cited

U.S. PATENT DOCUMENTS

| | | |
|---|---|---|
| 3,692,023 | 9/1972 | Phillips et al. . |
| 4,719,926 | 1/1988 | Nelson . |
| 5,354,597 | 10/1994 | Capik et al. . |
| 5,449,550 | 9/1995 | Yasis et al. . |

OTHER PUBLICATIONS

Smith and Nephew Casting, Cast Room Products, p. 3, 1994.

*Primary Examiner*—Richard J. Apley
*Assistant Examiner*—Kim M. Lee
*Attorney, Agent, or Firm*—Townsend and Townsend and Crew LLP

[57] ABSTRACT

A tape is used for the wrapping of ankles or other joints having a inelastic back in tension and a hypo-allergenic elastic for placement to the skin. Examples of the inelastic back can include tapes with metal or carbon fiber backings which essentially have no appreciable elasticity and deformation when applied over the skin at the ankle. In the preferred embodiment of this invention, the inelastic backing of the tape has a Young's modulus of elasticity exceeding 5 and is not subject to substantial elongation as placed over the ankle. Wrapping of the ankle with such tapes utilizing hypo-allergenic adhesives is disclosed with the tape being removable and reusable even by the athlete utilizing the ankle wrapping.

7 Claims, 6 Drawing Sheets

METHOD FOR JOINT TAPING WITH INELASTIC TAPE

This application is a continuation-in-part of Ser. No. 08/753,149, filed Nov. 20, 1996 now abandoned.

This invention relates to ankle bracing by taping of the ankle. More particularly, taping of the ankle is disclosed utilizing a tape with skin adhering hypo-allergenic adhesive having an essentially inelastic tensile backing. The tape is characterized by having a Young's modulus of elasticity of 5 or more. Reuse of the tape is possible with the athlete rendered capable of self application of tape.

BACKGROUND OF THE INVENTION

Ankle injuries are a very common injury especially in sports. It is estimated there is at least one ankle injury per 10,000 people per day in the U.S. Almost half of all basketball injuries are ankle injuries. About one-third of all soccer injuries are ankle injuries and one-fourth of volleyball injuries are ankle injuries. Some estimates indicate about one-third of all ankle sprains can result in some residual symptoms.

The primary concern as relates to ankles is to prevent both acute injuries and subsequent chronic functional instability. This functional instability may be characterized by complaints of a weak ankle or an unstable ankle with unpredictable giving way, chronic or recurrent sprains, difficulty when running on uneven surfaces or cutting or jumping in athletic activities.

There are two facets to the treatment of ankle injuries. The first is prevention of injuries, and the second is the treatment of the injury.

In reference to prevention, ankle taping has been shown to be effective in decreasing the incidence of ankle sprains in basketball players. The primary advantage of ankle taping is that it is extremely light weight and does not restrict any nominal range of motion.

Conventional tapes used for ankle taping have two distinguishing characteristics from the disclosure that follows. First, the tapes are elastic; they elastically stretch as placed on the skin. When the force is relieved, the tape (usually) returns to its former strength and tension around the ankle. Unfortunately, the elasticity reduces the effectiveness of the taping.

Second, the tapes non-elastically deform. In such deformation, the tapes stretch to a new length—and never elastically return to their old length. This is the greatest failing of such taping.

Problems with ankle taping relate to this elongation or deformation and to the fact that it gradually loses some of its effectiveness with progressive playing time. (Some estimates indicate it loses 40% of his effectiveness in the first hour of sport competition.)

Another problem with ankle taping is that it requires skill to apply the ankle tape and there is a certain amount of cost in taping the ankle on a regular basis. The cost is in the from of supplies and time spent by trainer.

On sports teams at the high school, college and professional level, professional trainers are available to provide the prophylactic taping, but recreational athletes and lesser programs typically do not have that option.

Taping or strapping and bracing are used to restrict undesired or potentially harmful motion but to allow desired motion. There are many types of tapes and bandages available to be used by athletes but only an adhesive tape is appropriate. Typically tape should be adhesive, strong, non-irritating and easy to work with.

Additional problems associated with tape application include reduced circulation if the tape is too tight, skin irritation due to mechanical or allergic phenomena and the fact that when placed under heavy strain, the tape may gradually lose its effectiveness. To maintain the desired support, it may be necessary to reapply the tape during breaks in athletic activity. The application of the tape is an acquired skill usually requiring an athletic trainer or someone else who has been properly trained.

At the present time, the only option to standard taping is some type of rigid brace. There are a number of different braces on the market. Some of them are lace up and others use VELCRO®. One of the most popular uses an air bladder between the brace and the skin, referred to as an Air Cast™. The advantage of the braces, are they are easy to take off and on. They do not require a trainer. They are adjustable. They are less likely to irritate the skin. Over time, they are less expensive than taping if taping is required for a lengthy period.

By comparison, bracing has certain advantages over taping and it does not require the same skill level to be applied. It is usually more convenient and over a long period of time can be more cost effective.

The disadvantages of the brace include slipping during use, the excess weight and problems with sizing. To increase the mechanical support, stronger, harder materials can be used. However, the more that is added the bulkier it becomes and the more it restricts desirable ranges of motion while limiting undesired motion.

Most athletes do not like the ankle brace and find it confining and awkward and frequently they feel it slows them down and limits their performance. Additionally, bracing does not provide the proprioception feedback from the skin that is the important part of taping but cannot be matched by a brace.

Regarding the proprioceptional feedback, it is believed that tape acting on skin sends a signal to muscle surrounding the ankle to resist bending of the ankle. The reaction of the muscle is an important function of ankle taping.

SUMMARY OF THE INVENTION

A tape is used for the wrapping of ankles or other joints having a inelastic back in tension and a hypo-allergenic elastic for placement to the skin. Examples of the inelastic back can include tapes with metal or carbon fiber backings which essentially have no appreciable elasticity and deformation when applied over the skin at the ankle. In the preferred embodiment of this invention, the inelastic backing of the tape has a Young's modulus of elasticity exceeding 5 acting in the longitudinal direction of the tape and is not subject to substantial elongation (over 1%) as placed over the ankle. Wrapping of the ankle with such tapes utilizing hypo-allergenic adhesives is disclosed with the tape being removable and reusable even by the athlete utilizing the ankle wrapping.

The tape being "inelastic" conforms to properties not found with conventional adhesive tapes. First, any elastic stretching of the tape occurring with the ankle wrapping must occur within the limits of Hooke's law. The elastic action of the tape in tension in the longitudinal direction versus elongation is a straight line (within the range of elasticity defined by Hooke's law) with the ratio of stress to strain (elongation) being Young's modulus in excess of 5. Thus the Young's modulus of elasticity required falls in the range of that elasticity provided at least by metals. Further, the tape cannot be subject to any kind of permanent elongation under the tensile forces applied by the wrapped ankle to the tape.

From this requirement that Young's modulus be in excess of 5, it will be seen that metal backed tapes can be used. For example, the following metals (followed by the exemplary Young's modulus) can be utilized as a tape backing; magnesium alloys (6.3), aluminum (9.9 to 10.3), brass (15.9) and steel (28–30).

It will be understood that this is to be compared with conventional adhesive tape. Conventional adhesive is anisotropic. Such conventional adhesive tape has a Young's modulus well below 5.

Likewise, modern so-called graphite fibers in either a woven or linear array can be stressed in tension. Any of these fibers having a Young's modulus in excess of 5 may be used. For example, typical graphite fiber composites have tensile modulus of elasticity in the range of 5–10. For example, Thornel® VCC-20®, a product of the Union Carbide Company has a tensile modulus in the range of 5.7.

Additionally Hexel FBT-272 has a tensile modulus in the range of 10. Others may readily be identified by the user.

Secondly, the tape must be sufficiently flexible to permit wrapping. As a consequence, tapes that permanently break or shatter when wrapped about an ankle joint cannot be used.

Thirdly, the tape must have an adhered adhesive capable of fastening to the skin. It does not matter whether the adhesive adheres directly to the metal or fiber backing or makes use of an intermediate layer(s). What is required is that the essentially inelastic backing impart to the overall tape a Young's modulus exceeding 5 when the tape is stressed in the longitudinal direction so that no appreciable elasticity or stretching of the tape occurs. Likewise, elongation or permanent deformation of the tape must not occur once the ankle is wrapped.

It is important to understand the interaction between the wrapping with the tape of high tensile strength and the human skin over the ankle. Specifically, when an ankle is conventionally taped, and then placed under strain—as where a basketball player is actively playing—the muscle around the ankle responds to loading on the skin through taping. It is found that where taping is fresh—and not stretched—loading of the skin and reaction of muscle to counter act strain occurs early. Where tape has elongated, this muscle reinforcing action is delayed. By the expedient of utilizing an essentially non-elastic tape which does not materially elongate, the muscle reinforcing reaction occurs early—and the desired reinforcement of the tape to the joint is prolonged.

DESCRIPTION OF THE PREFERRED EMBODIMENT

Figure 1:
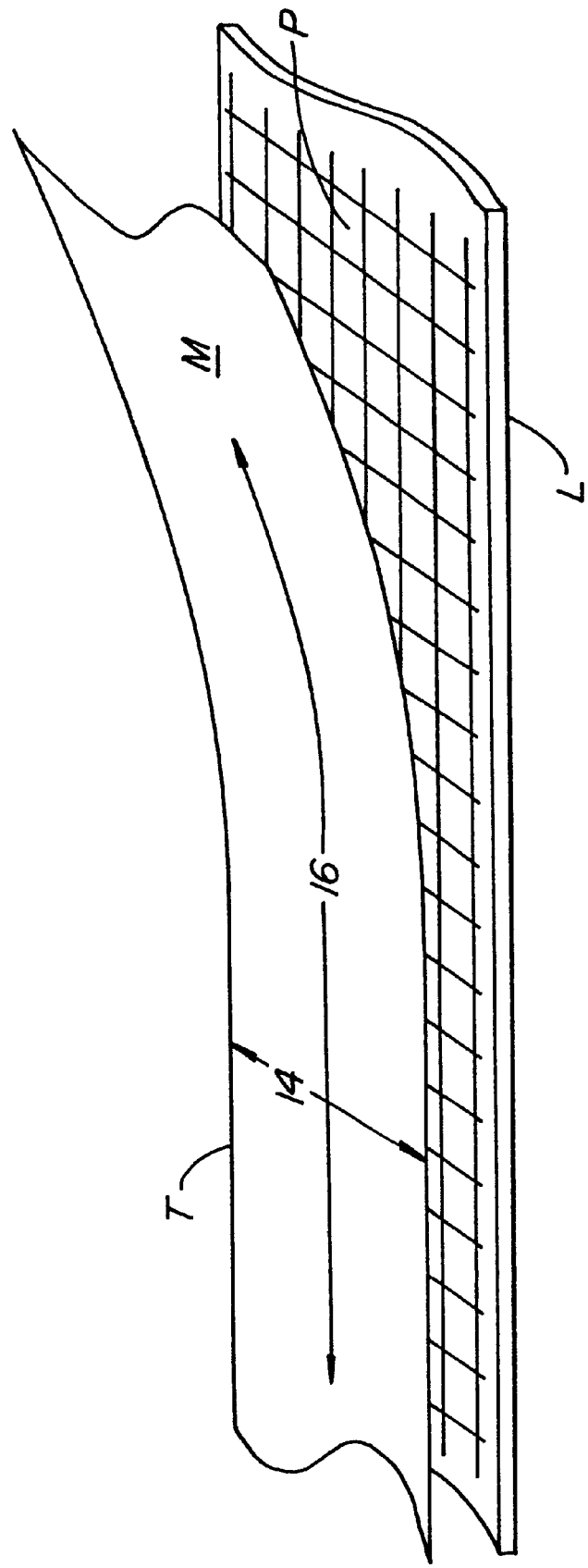
FIG. 1 is a segmented view of tape which can be used or the taping of this invention, the tape here being illustrated with a metal backing.

Referring to FIG. 1, tape T is illustrated. Tape T includes metal backing M which is preferably aluminum foil of approximate 0.005 inches thickness. Underlying metal backing M there is plastic layer P having hypo-allergenic adhesive layer L for exposure to the skin. Tape T has width 14 and is elongate along longitudinal axis 16.

Figure 2:
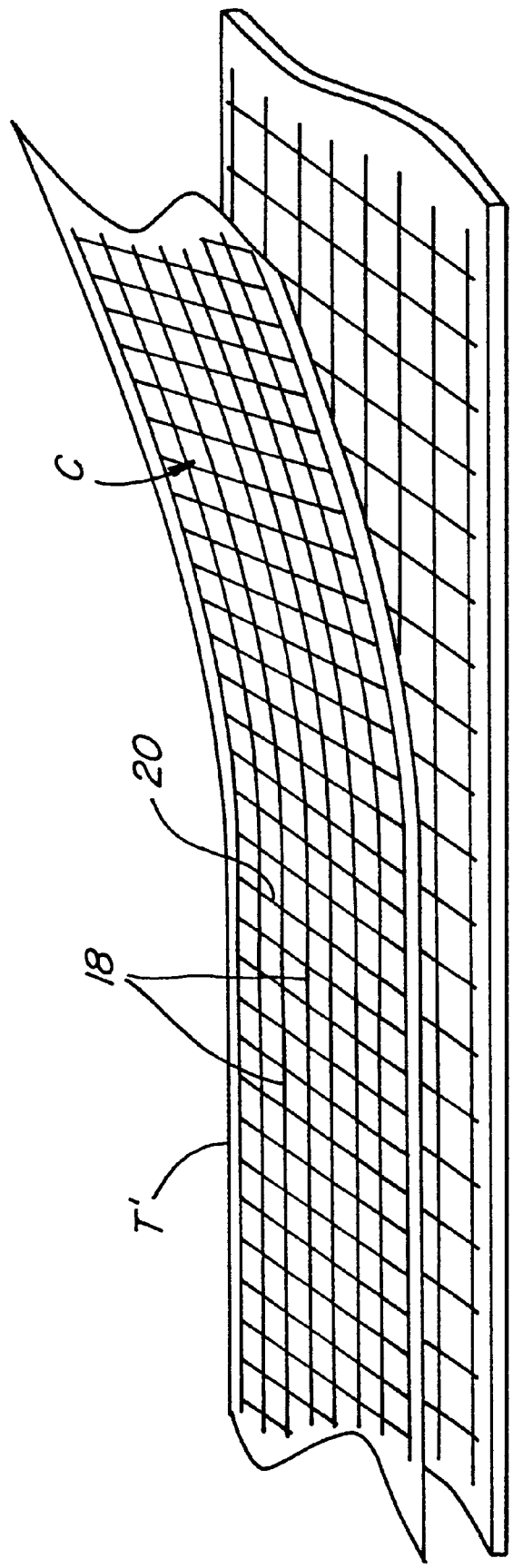
FIG. 2 is a segmented view of tape which can be used for taping of this invention, this view being similar to FIG. 1 but illustrating the use of a composite material with two sided adhesive tape for adhering the tape to an ankle.

FIG. 2 is another example illustrating tape T'. In this case graphite fiber material cloth C having warp threads 18 extending longitudinally and weft threads 20 extending across tape T'. Warp threads 18 are made of graphite carbon fiber with the tow of the fiber running in the longitudinal direction of the tape. Weft threads 20 can likewise be made of the same material; however, this is not required.

It will be understood that graphite fibers can have their respective warp and weft threads run other than in the longitudinal and width direction of the tape. It is only required that the tape have the required Young's modulus in excess of 5 longitudinally of the tape.

Figure 3:
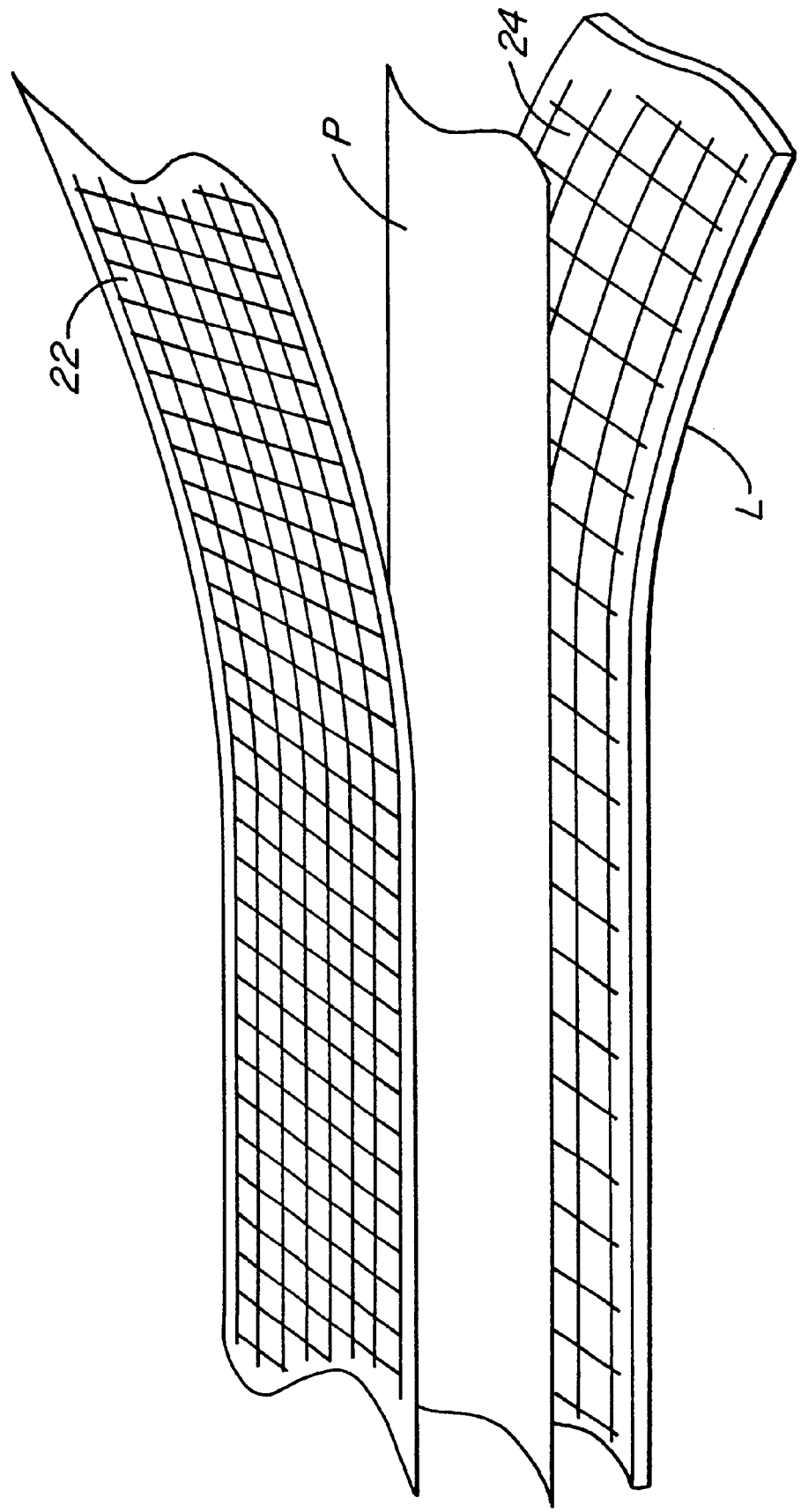
FIG. 3 is a segmented view of tape which can be used for taping of this invention, this view showing a tape having three discrete layers; and, FIG. 4 is a view of an ankle being taped with the so-called stirrup being applied.

Finally, and referring to FIG. 3, plastic layer P has adhesive on both sides. graphite carbon fiber tape 22 is adhered to one side; conventional cloth tape 24 is adhered to the opposite side. This conventional cloth tape 24 has the bottom skin exposed side coated with hypo-allergenic adhesive layer L.

Regarding the hypo-allergenic adhesive, such adhesives are used on Aspen Return Monitor Dual, sold under the stock number 60-7203-002 Conmed Inc., Division Aspen Surgical Systems of Utica N.Y. 13501. Specifically, any tape which fits to the leg with such a hypo-allergenic adhesive will suffice for the practice of this invention.

Having given three examples of tapes that can be used, the process of applying the tape to the ankle of a patient can now be described.

Figure 4:
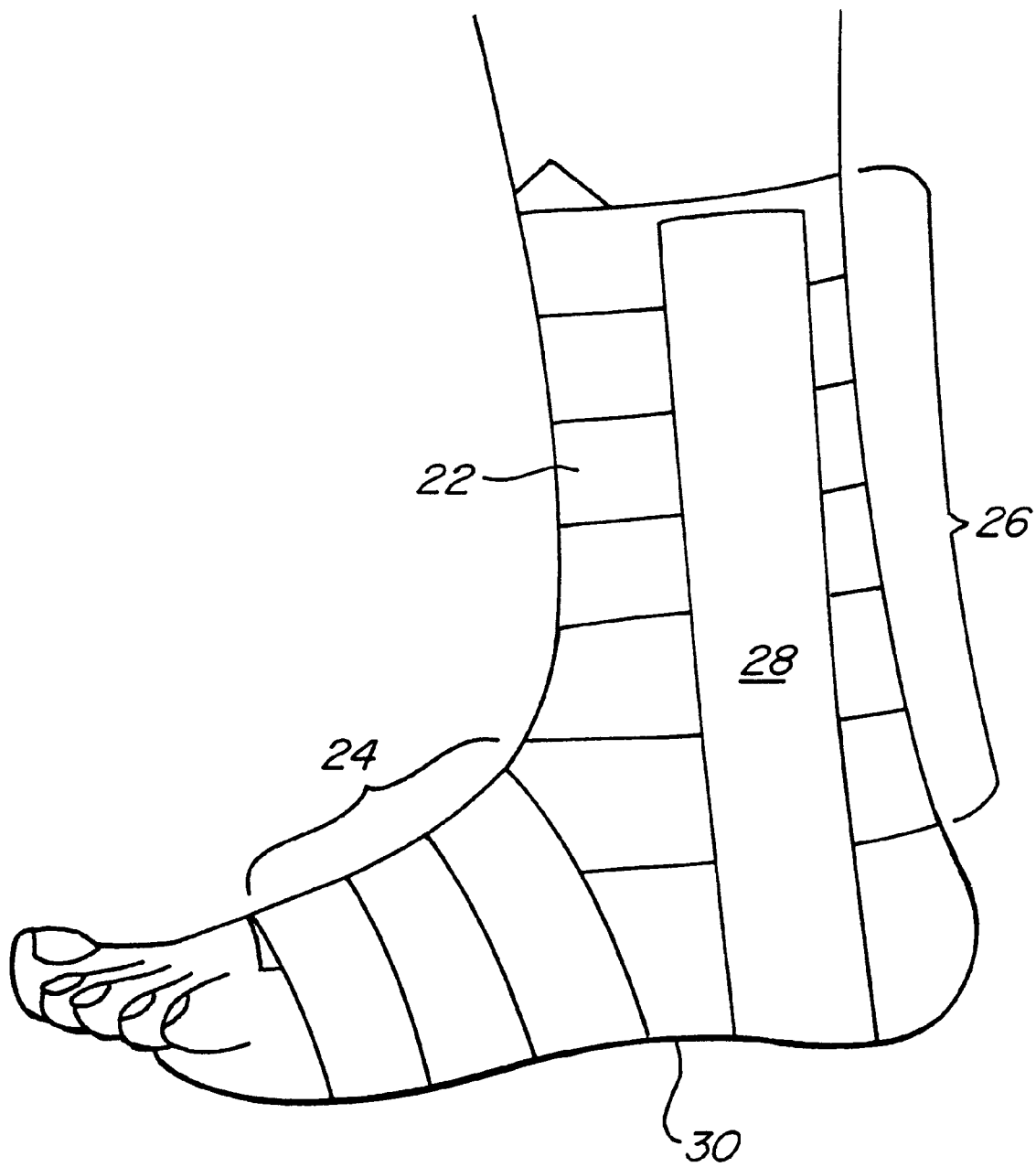
Figure 5:
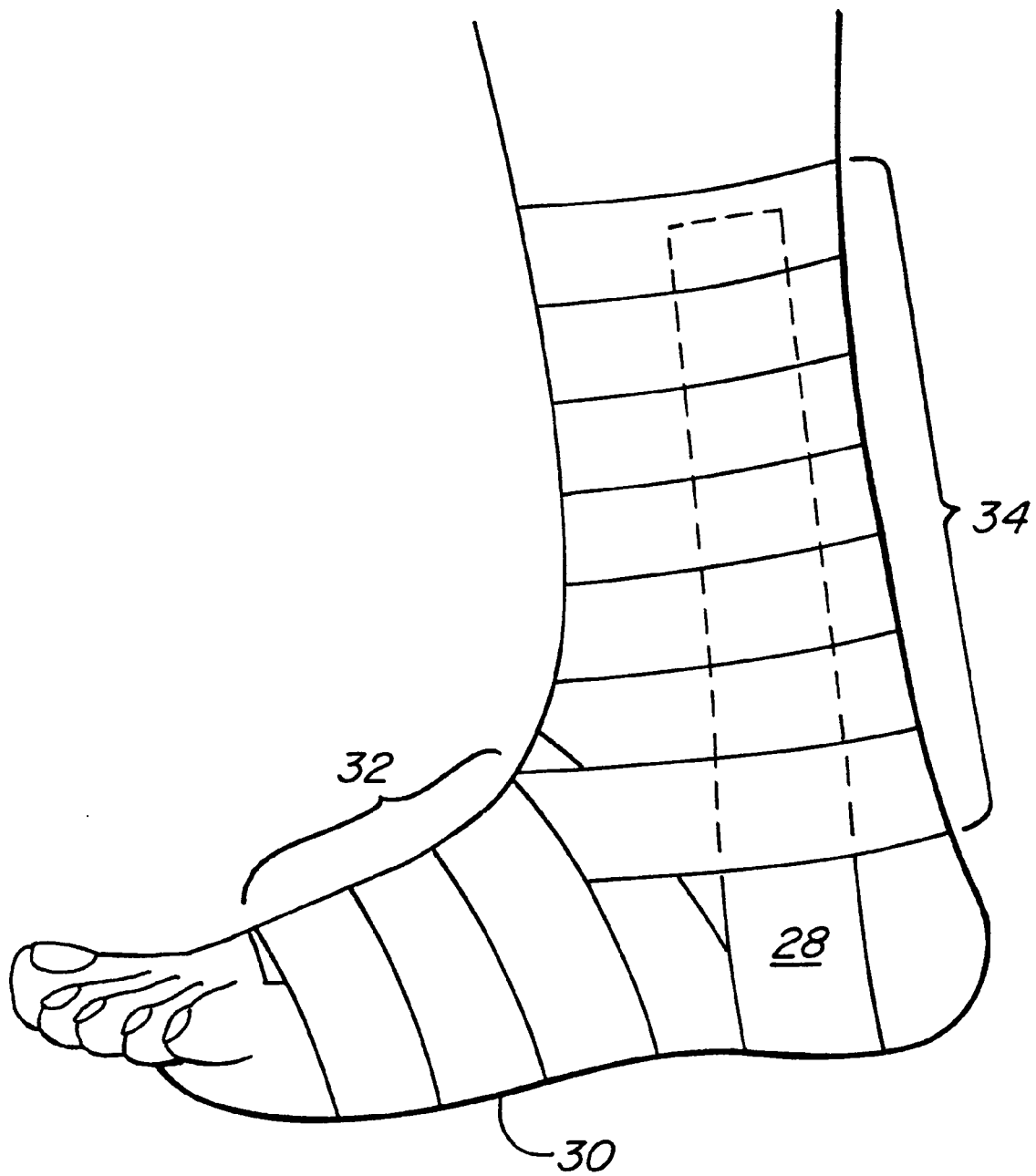
FIG. 5 is a view of the ankle of FIG. 4 fully taped showing in broken lines the final placement of the stirrup; and, FIG. 6 is a perspective view of a hand illustrating the thumb in the vicinity of the "MP" meta phalendl joint being secured by the technique of this invention.

Referring to FIGS. 4 and 5, the application of the tape of this invention to a typical ankle taping is shown. Specifically, the ankle is first taped with a so-called preparatory tape 22 commonly referred to as "prowrap." Preparatory tape 22 is shown binding ankle A in two discrete spirals; foot spiral 24 and ankle spiral 26.

Thereafter, stirrup 28 is applied over sole 30 from mesial to distal if the injury is on the distal side and from distal to mesial if the injury is on the mesial side. In this particular wrapping, the backing of stirrup 28 is provided with the tape of this invention shown in FIGS. 1–3.

Referring to FIG. 5, completion of the taping is shown. Specifically, stirrup 28 is over wrapped with conventional adhesive tape foot spiral 32 and conventional adhesive tape ankle spiral 34.

With the wrapping of FIG. 5, superior resistance to stretching of the wrapping is provided.

Figure 6:
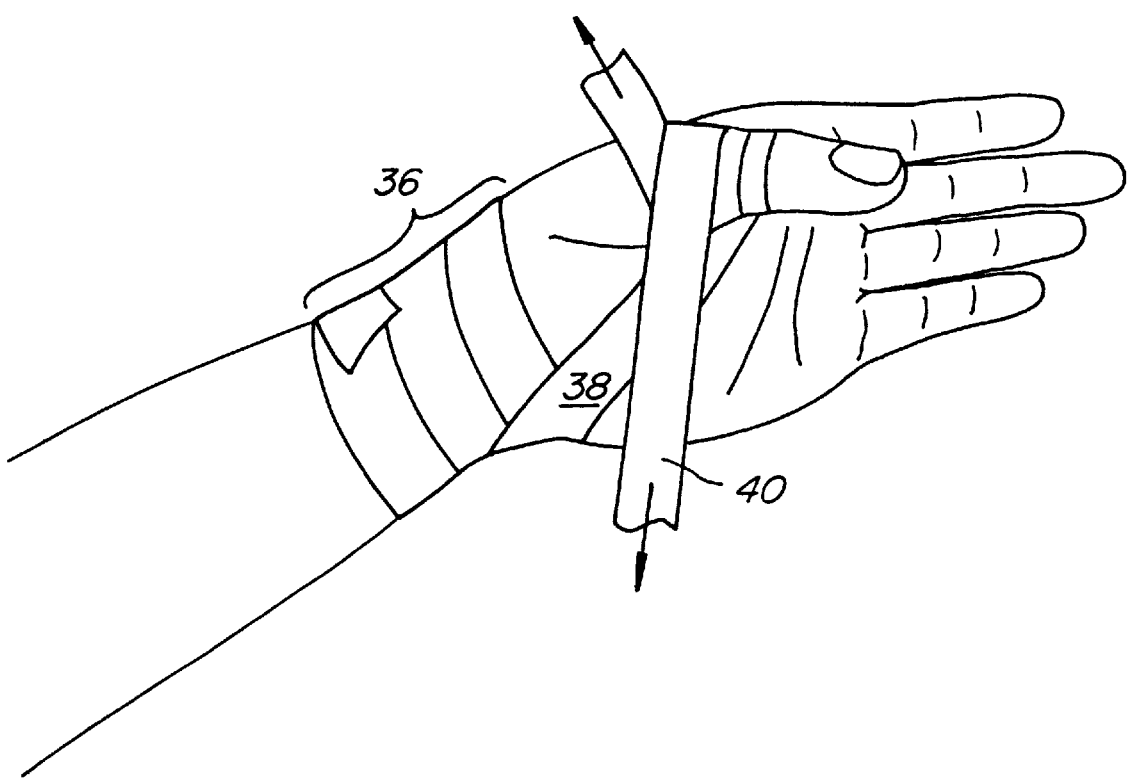

It is not required that wrapping be restricted to the ankle. Referring to FIG. 6, taping of the hand is shown for so-called "thumb sprain taping" of the so-called "MP" meta phalendl joint. Wrist spiral 36 and hand spiral 38 are applied. Thereafter, and as relevant to the disclosure herein, a so-called incomplete figure-8 strip 40 is applied to the thumb above the joint to the hand. The tape utilized is that illustrated in FIGS. 1–3 having the hypo-allergenic adhesive. The respective tape ends are firmly anchored, leaving a wrapping of the joint in accordance with this invention.

In understanding this invention, it is important to characterize the tape that is used. In the data below, I compare so-called standard adhesive tape with the tape used herein. As the reader can readily determine—the resulting tape is comparative inelastic—making possible the result produced by this invention.

Elastic/Creep Testing of Athleteic Tape

Three rolls of 1½" width standard brand (Curity-Kendall) athletic tape and samples of a prototype (U.S. Patent Pending) inelastic tape were submitted to evaluate their elastic properties, including creep measurements. In order to obtain some general information on the prototype inelastic tape, a sample was pulled in tension. Based on this test, it was determined that the elastic limit, initial deviation from the straight portion of the curve, occurred at 27.5 lbs. Using this information, a load of 75% of 27.5 lbs. of 20.6 lbs. was selected to determine the creep properties of the samples. The following results were obtained on the standard brand tape after 10 minutes:

| Sample | Creep (in.) |
| --- | --- |
| Std. Brand Tape 1 | 0.014, 0.014 |
| Std. Brand Tape 2 | 0.014 |
| Std. Brand Tape 3 | 0.016 |

Due to the nature of the adhesive on the prototype inelastic tape, gripping the tape for creep measurements proved quite difficult. After several trials, it was determined that the adhesive had to be removed before the tape could be gripped for testing. The creep measured on the inelastic tape thus prepared was 0.001" after 10 minutes.

The reader will understand that I have shown examples of tapings in which only one member—the stirrup in the case of the ankle and the partial figure-8 in the case of the thumb (at the MP joint)—are the only sections of the taping made from the inelastic tape here disclosed. The reader will understand that the whole bandage or any key part thereof can be made from the inelastic tape here disclosed.

What is claimed is:

1. A method of taping a joint comprising the steps of:
    providing a joint with skin about the joint;
    providing a flexible tape having a longitudinal major axis with a minor axis extending from side to side of the flexible tape, the flexible tape having an inside surface for exposure to the skin;
    attaching to the flexible tape a flexible material having a Young's tensile modulus greater than 5 with substantially no elongation, the flexible material having a Young's tensile modulus greater than 5 fully extended along the longitudinal major axis of the flexible tape to resist tensile expansion at least along the longitudinal major axis of the flexible tape while maintaining the tape and flexible material flexible at all times;
    adhering a skin adhesive to the inside surface of the flexible tape;
    wrapping and adhering the skin adhesive and flexible tape on the skin about the joint under tension exerted along the longitudinal major axis of the flexible tape to reinforce the joint with the flexible tape and flexible material having a Young's tensile modulus greater than 5 with substantially no elongation.

2. The method of taping a joint according to claim 1, wherein the attaching step includes:
    providing the tape with fully extended fibers having a tensile component along the longitudinal major axis of the tape with a Young's modulus in excess of 5.

3. The method of taping a joint according to claim 1 wherein the attaching step includes:
    providing the flexible tape with fully extended fibers having a tensile component along the longitudinal major axis of the flexible tape with a Young's modulus in excess of 5.

4. The method of taping a joint according to claim 1 wherein the attaching step includes:
    placing a backing on an outside of the flexible tape.

5. The method of taping a joint according to claim 1 wherein:
    the step of adhering a skin adhesive to the inside surface of the tape includes adding a hypo-allergenic non-inflammatory adhesive.

6. The method of taping a joint according to claim 1 wherein:
    providing an ankle joint;
    wrapping the ankle with a flexible stirrup; and,
    over wrapping the stirrup with the flexible tape.

7. The method of taping a joint according to claim 1 wherein:
    the step of adhering a skin adhesive to the inside surface of the flexible tape includes adding a hypo-allergenic non-inflammatory adhesive.

* * * * *